US00PP07962P

United States Patent [19]

O'Brien et al.

[11] Patent Number: Plant 7,962

[45] Date of Patent: Sep. 8, 1992

[54] MINIATURE ROSE PLANT NAMED 'YANTAI'

[76] Inventors: D. Bennett, deceased, late of Chula Vista, Calif., by Susan Mae O'Brien, Administrator

[21] Appl. No.: 636,391

[22] Filed: Dec. 31, 1990

[51] Int. Cl.[5] ..... A01H 5/00

[52] U.S. Cl. ..... Plt./8.2

[58] Field of Search ..... Plt. 7, 8

*Primary Examiner*—James R. Feyrer

[57] ABSTRACT

The subject of the present disclosure is a new and distinct variety of miniature rose plant, named 'YANTAI', which is characterized by pale yellow blooms with a deeper yellow center, ranging from near Mimosa Yellow to near Empire Yellow with an occasional pale pink blush on the outer petals ranging from near French Rose to near Venetian Pink. Blooms of this rose are usually borne one to a stem with hybrid tea form but on occasion may be produced in sprays of 3 to 5 or more. The bush is vigorous, well-branched and produces moderate to heavy quantity of blooms.

1 Drawing Sheet

The present invention relates to a new and distinct variety of a hardy, dwarf, bush plant of the miniature class; the variety being primarily characterized as yellow blend.

The variety is further characterized by:

Long stemmed blooms of hybrid tea-type form, borne usually one to a stem but on occasion in sprays of 3 to 5 or more. The blooms are held very erect and well above the foliage.

The plant range in height from 18 to 24 inches (45 to 60 cm). The canes are sturdy and erect with moderate branching and medium to heavy foliage covering. The plant is a moderate to heavy bloomer that does well either in the greenhouse or outdoors.

The plant has good growth habits, well-shaped and attractive, bearing numerous leaflets of average size. I have found this variety to be easily asexually reproduced from cuttings.

The seed parent was Portrait (U.S. Plant Pat. No. 3,097), and the pollen parent was Party Girl (U.S. Plant Pat. No. 4,598). It differs from its seed parent in the following ways. It is a miniature rose in yellow blend, and Portrait is a hybrid tea in pink blend. It differs from its pollen parent in the following ways. It produces larger blooms with pale yellow outer petals and a center of deeper yellow, and Party Girl produces blooms that are one shade of pale yellow with a blush of pink on all petals and has a smaller bloom size.

The single color photographic view shows, in plan view, a bouquet of 'Yantai' in various stages of maturity from bud stage to nearly open bloom stage.

The descriptive matter which follows pertains to roses grown and color values observed in plants and newly opened blooms in the months of March through November 1990. The plants were grown outdoors in Chula Vista, Calif., and are believed to be accurate standards for this cultivar in similar conditions of soil and climate elsewhere.

Referring now specifically to the new and distinct variety of miniature rose plant named 'Yantai', the following is a detailed description thereof in outline; all major color plate identifications being by reference to The British Colour Council Horicultural Chart, except where common terms of color definition are employed.

Type: Hardy, dwarf, bushy, greenhouse or outdoor, exhibition or garden decorative potted plant.

Class: Miniature.

Variety name: Yantai.

Flowers borne: Usually one to a stem, but occasionally in sprays of 3 to 5 or more on erect stems with foliage well below the blooms.

Quantity of bloom: Moderate to heavy both outdoors or greenhouse grown.

Bud:

*Peduncle.*—Average length (30 to 50 mm); average diameter and sturdy; ranging from near Scheeles Green (860/3 to 860/1 page 176) with occasional tinting of bronze.

*Hairs.*—Extremely small and sparse with a reddish color; located over the surface of the peduncle and calyx tube.

*Calyx.*—Color range same as peduncle.

*Opening.*—Opens well in all weather.

Bloom:

*Size when fully open.*—Average for a miniature variety (30 to 40 mm).

*Petalage.*—Double — 25 to 30 petals, arranged regularly, plus 5 to 10 petaloids.

*Form.*—Urn-shaped to ovoid as the bloom opens. The petals remain somewhat cupped with the apex and/or margins reflexed outward, becoming at maturity more loosely cupped.

Petals: Fairly thick with good substance; both the upper and under surfaces of all petals have a matte finish.

*Shape.*—Outer petals are of a broad obovate form. The intermediate petals are very much like the outer petals only narrower. The inner petals are a broad lanceolate form; and the petaloids are also lanceolate with some occasional irregularities.

Color: Newly opened flowers from plants grown outdoors (March through November of 1990), Chula Vista, Calif.

*Outer petals.*—Upper Surfaces — Ranging from near Mimosa Yellow (602/3 to 602/2 page 143) to near Empire Yellow (603/3 to 603/2 page 66) with occasional blush ranging from near French Rose (520/3 page 136) to near Venetian Pink (420/3 page 125).

*Intermediate Petals.*—Upper Surfaces — Ranging from near Mimosa Yellow (602/2 to 602/1 page 143) to near Empire Yellow (603/2 to 603/1 page 66).

*Inner petals.*—Upper Surfaces — Ranging from near Mimosa Yellow (602/1 to 602 page 143) to near Empire Yellow (603/1 to 603 page 66).

*All petals.*—Under Surfaces — Slightly lighter tones to upper surfaces.

*General color effect.*—Newly opened flowers — Pale yellow with a slightly deep yellow center and occasional blush of pale pink on outermost petals. After 2 to 3 days open — Slight fading of all colors.

*Flower longevity.*—(March through November 1990) Plant in pot 5 to 7 days from bud with sepals reflexed to fully open bloom. Holding at fully opened for 3 to 5 days longer. Cut bloom at living room temperature 7 to 10 days or longer.

Reproductive organs:

*Stamens.*—A generous amount arranged uniformly around the pistil.

*Filaments.*—Varying in length with shorter filaments more proximal to the pistil; pale yellow in color with anthers of golden yellow.

*Pollen.*—Abundant.

*Pistil.*—Short, spreading and abundant; pale yellow to reddish at the cap.

*Ovaries.*—All encased in calyx.

*Hips.*—Some.

*Seeds.*—3 to 5 or more in each hip.

*Sepals.*—Permanent; spear-shaped; open as the bloom opens, recurving against the peduncle, when the bloom is fully opened.

Foliage:

*Leaves.*—5 to 7 leaflets on average; medium size for a miniature rose plant.

*Leaflets.*—Broad ovate-shaped.

*Margins.*—Very serrated with tinting of bronze, especially noticeable on the newer foliage.

*Color.*—Ranging from near Scheeles Green (860/3 to 860/1 page 175) to near Lettuce Green (861/2 to 861 page 176) with occasional bronzing of the margins, especially on the newer foliage. Upper surfaces have a semi-glossy finish, and the under surfaces have a matte finish of a slightly lighter shade than the upper surfaces.

*Rachis.*—Medium strength; upper surface is grooved with very small hairs over the length of it. Under surface has few if any hairs but does contain 2 to 5 small thorns.

*Stipules.*—Varying in length from small to medium; average width; tapering auricles angled outward at about 45 degrees.

Growth:

*Habit.*—Dwarf, at 18 to 24 inches, tall to bush; average for a miniature rose plant.

*Growth.*—Vigorous and well-branched.

*Canes.*—Medium diameter; sturdy; held erect.

*Main stems.*—Color range same as foliage.

*Thorns.*—Averaging less than 5 to 10 per 10 cm on the main stems and branches. Pale yellow with a reddish base; average size; slender and straight.

*Branches.*—Color range same as foliage.

The miniature rose plant and its flowers as herein described may vary in slight detail due to climate, soil and cultural conditions under which the variety may be grown; the present description being of the variety as grown in Chula Vista, Calif.

The following is claimed:

1. A new and distinct variety of miniature rose plant, named 'Yantai', of hardy, dwarf, vigorous growth, well-branched and attractive in appearance, substantially as illustrated and described, characterized by long stems bearing hybrid tea-type pale yellow blooms with a deeper yellow center ranging from near Mimosa Yellow to near Empire Yellow with an occasional pale pink blush on the outer petals ranging from near French Rose to near Venetial Pink; producing a moderate to heavy quantity of blooms; and, as forming blooms in a size range of from substantially 30 mm to 40 mm in diameter.

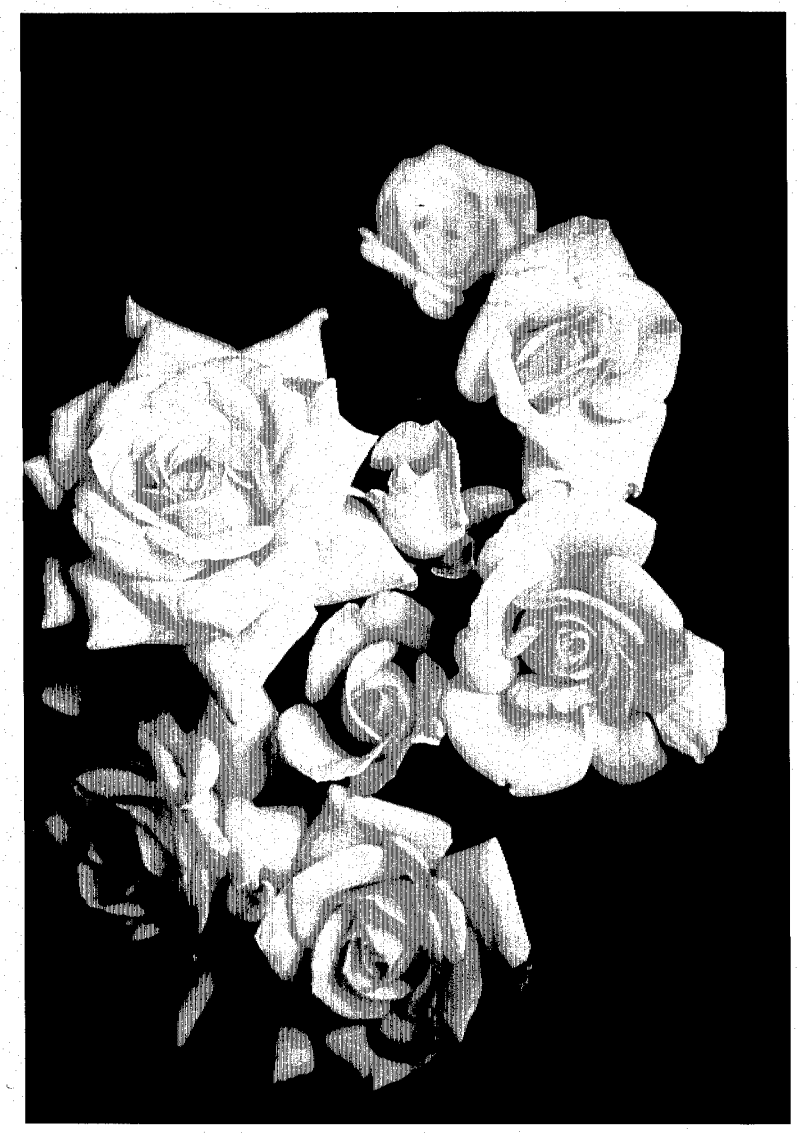

* * * * *